(12) United States Patent
Jones

(10) Patent No.: US 10,041,913 B2
(45) Date of Patent: *Aug. 7, 2018

(54) ONE REACTOR POST COLUMN REACTION GC/FID SYSTEM USING RU CATALYST

(71) Applicant: Activated Research Company, LLC, Eden Prairie, MN (US)

(72) Inventor: Andrew Jones, Minneapolis, MN (US)

(73) Assignee: Activated Research Company, LLC, Eden Prairie, MN (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/984,801

(22) Filed: Dec. 30, 2015

(65) Prior Publication Data

US 2016/0187307 A1    Jun. 30, 2016

Related U.S. Application Data

(60) Provisional application No. 62/098,721, filed on Dec. 31, 2014.

(51) Int. Cl.
*G01N 30/68*     (2006.01)
*G01N 30/88*     (2006.01)
(Continued)

(52) U.S. Cl.
CPC ............ *G01N 30/68* (2013.01); *B01J 23/462* (2013.01); *G01N 30/88* (2013.01);
(Continued)

(58) Field of Classification Search
CPC .. G01N 30/68; G01N 30/88; G01N 2030/884; G01N 2030/025; G01N 30/04;
(Continued)

(56) References Cited

U.S. PATENT DOCUMENTS

| 2004/0077903 A1* | 4/2004 | Suzuki | C07C 249/04 564/267 |
| 2008/0064769 A1* | 3/2008 | Sato | B01J 23/6562 518/717 |

(Continued)

FOREIGN PATENT DOCUMENTS

| EP | 1061365 | 12/2000 | |
| EP | 1061365 A1 * | 12/2000 | ........... G01N 30/466 |
| EP | 1719555 | 11/2006 | |

OTHER PUBLICATIONS

Carbon Dioxide Methanation on a Ruthenium Catalyst, by Lunde et al., Ind. Eng. Chem., Process Des. Develop.,vol. 13, No. 1, 1974, pp. 27-33.*

(Continued)

*Primary Examiner* — Manish S Shah
*Assistant Examiner* — Suman K Nath
(74) *Attorney, Agent, or Firm* — E. Joseph Gess

(57) ABSTRACT

Provided is a system comprising a conduit from a gas chromatograph column to a reactor comprising a Ru catalyst, with a hydrogen feed conduit for providing hydrogen to the conduit from the gas chromatograph column, and a conduit from the reactor to an FID detector. This allows one to practice a method for the detection and quantification of organic molecules from a gas chromatograph which comprises passing the effluent from a gas chromatograph column to a reactor comprising a Ru catalyst; adding hydrogen to the effluent prior to the effluent reaching the catalyst; reacting the effluent from the gas chromatograph column in the reactor to reduce all organic containing molecules to $CH_4$ by heating to an elevated temperature, and passing the effluent from the reactor to an FID.

9 Claims, 2 Drawing Sheets

(51) Int. Cl.
*B01J 23/46* (2006.01)
*G01N 30/02* (2006.01)

(52) U.S. Cl.
CPC ... *B01J 2531/821* (2013.01); *G01N 2030/025* (2013.01); *G01N 2030/884* (2013.01)

(58) Field of Classification Search
CPC ... G01N 30/06; B01J 23/462; B01J 2531/821; Y10T 436/25875
USPC ........ 73/23.41, 23.42, 23.35; 422/89; 95/82, 95/161; 436/159; 518/702, 715, 717
See application file for complete search history.

(56) References Cited

U.S. PATENT DOCUMENTS

| | | | |
|---|---|---|---|
| 2013/0102693 A1* | 4/2013 | Kibby | C10G 2/332 518/715 |
| 2013/0210936 A1* | 8/2013 | Zhou | C07C 45/41 518/702 |

OTHER PUBLICATIONS

Lunde et al., "Kinetics of Carbon Dioxide Methanation on a Ruthenium Catalyst", Am. Chem. Soc., Div. Fuel Chem., Prepr, Dec. 31, 1974 (Dec. 31, 1974), pp. 11-27.
International Search Report from corresponding Application No. PCT/US2015/068137 dated Mar. 31, 2016.

* cited by examiner

ONE REACTOR POST COLUMN REACTION GC/FID SYSTEM USING RU CATALYST

CROSS REFERENCE TO RELATED APPLICATIONS

Priority is hereby claimed to Provisional Patent Application No. 62/098,721, filed Dec. 31, 2014, which is hereby incorporated by reference in its entirety.

BACKGROUND

Gas chromatography (GC) is a useful technique for the separation and quantification of molecules. The detection and quantification of organic molecules from a GC is commonly carried out by flame ionization detection (FID) because of its high sensitivity to carbon. The FID operates by ionizing a fraction of the carbon containing molecules and measuring the resulting number of ions with a current collector. The fraction of ionized carbons depends on the number and nature of carbon atoms in a molecule, including the number and types of bonds of each carbon atom (e.g., carbonyl, aldehyde, ether). Methane ($CH_4$) has the highest per carbon sensitivity in the FID because of its four bonds to hydrogen; carbons that contain double/triple bonds or bonds to elements other than H decrease the fraction of ionized carbons created in the FID, and thereby decrease the sensitivity of the FID for that molecule on a per carbon basis. The decreased sensitivity of the FID to various molecules requires that the response of the FID to each molecule be determined through laborious calibrations in order to accurately quantify the amount of a molecule in a sample. In some instances the sensitivity of the FID to the molecule is so low that it is effectively undetectable. These molecules usually have a large heteroatom content and include carbon monoxide (CO), carbon dioxide ($CO_2$), carbon disulfide ($CS_2$), carbonyl sulfide (COS), carbon tetrachloride ($CCl_4$), hydrogen cyanide (HCN), formamide ($CH_3NO$), formaldehyde ($CH_2O$) and formic acid ($CH_2O_2$). The decrease in carbon sensitivity of non-methane molecules and the laborious requirements of calibration reduce the utility of the FID detector and the GC in general.

The chemical conversion of a molecule into methane after its separation in the GC, but before its detection in the FID, increases the sensitivity of the detector to the molecule and eliminates the need for the calibration of its relative response factor to methane because all molecules are detected as methane. The conversion of GC effluents to methane can be accomplished a variety of ways with varying results and ease.

In one such embodiment the GC column effluent is combusted to $CO_2$ (and byproducts) and then reduced to $CH_4$ (and byproducts) in two separate reaction vessels separated by a 4-port valve and tubing (T. Watanabe et al., *Chromatography*, 27 (2006), pp. 49-55; T. Watanabe et al., *Talanta*, 72 (2007), pp. 1655-1658). The combustion reaction utilizes a commercially available palladium-asbestos catalyst packed into a stainless steel tube containing quartz wool. The reduction reaction utilizes a commercially available nickel catalyst packed into a stainless steel tube containing quartz wool. This setup involves the flow control of oxygen and hydrogen streams into a mixing point before the catalytic reduction zone of the reactor leading to a possibly dangerous and explosive mixtures of gases. There are separate temperature controls and heating elements for the combustion and reduction chambers. The effluent of the reduction reactor is fed to the FID.

Another example comprises a similar sequential reaction system of stainless steel tubes utilizing commercially available catalysts consisting of 10% palladium on alumina for the combustion chamber, and nickel on diatomaceous earth catalyst for the reduction chamber (S. Maduskar et al., *Lab on a Chip*, 15 (2015), pp. 440-447).

In another embodiment, using a single reaction scheme, a commercially available Ni catalyst is packed into a stainless steel tube and heated to 375° C. with hydrogen to convert carbon monoxide (CO) and carbon dioxide ($CO_2$) to methane, currently offered by Agilent Technologies. Another example of a $CO/CO_2$ to methane conversion reactor is offered by SRI Instruments and involves a packed metal tube (jet) that is inserted directly into the FID and heated to 380° C. with hydrogen. These reactors are designed for the sole conversion of $CO/CO_2$ to methane and Ni is easily poisoned by sulfur or excessive moisture or oxygen.

SUMMARY

Disclosed herein is a single-component device for the hydrogenolysis and reduction of GC column effluent streams to methane to increase the sensitivity of FID detection for select molecules and eliminate the need for the calibration of relative response factors. It has been found that with Ru as a catalyst at the appropriate temperature, one can avoid the two-step combustion-reduction reactor described in the prior art and convert many organic molecules to methane in a single-step reactor. The system and device as disclosed herein eliminates oxygen handling, oxygen flow control, and combustion reactor equipment found in two-step systems. It eliminates the explosive hazard of $O_2/H_2$ mixtures by removing the oxidation reactor. The reduction in reactor volume leads to increased peak resolution in the FID and significant cost savings. The Ru catalyst is more reactive and robust than the Ni catalysts used in the single reactor designs of the prior art resulting in longer catalyst lifetime, —and the ability to convert and thereby analyze, molecules other than just CO and $CO_2$, including formaldehyde and formic acid. The higher reactivity of Ru allows for more compact designs that lead to better separation performance and higher capacity.

Among other benefits, the present system offers several improvements on the prior art. It allows for the conversion of many molecules beyond just $CO/CO_2$ in a single reaction step with the addition of only hydrogen. This minimizes fittings, catalysts and complexities of multi-reactor setups. The absence of air eliminates the potentially dangerous (explosive) combination and catalytically undesirable mixture of hydrogen and oxygen in confined tubes. The use of Ru as the catalyst enables the complete conversion of a wide variety of molecules with long reactor lifetime and minimal impact on GC performance. Ru is highly resistant to poisoning and enables the detection of molecules that previously irreversibly deactivated other systems. The reactor design is small and compact to eliminate dead volume and improve flow dynamics for optimum performance. The entire component is designed within a single metal block to minimize fittings and improve heat transfer and flow dynamics.

DETAILED DESCRIPTION OF EMBODIMENTS

Provided herein is a system comprising a conduit from a gas chromatograph column to a component comprising a Ru catalyst. The system also comprises a hydrogen feed conduit for providing hydrogen to the component and a conduit from the component comprising the Ru catalyst to an FID detector. The catalyst comprises Ru metal or Ru on a catalyst support. The catalyst support can be any catalyst support, such as alumina or silica. By using the inventive one reactor system, one can safely practice a method for the detection and quantification of organic molecules from a gas chromatograph.

The process comprises passing the effluent from a gas chromatograph column to a component, which contains channels comprising a Ru catalyst. Hydrogen is added to the effluent within the component but prior to the effluent reaching the catalytic zone. The effluent from the gas chromatograph column is reacted over the catalyst to reduce carbon containing molecules to methane by heating to an elevated temperature. The effluent of this reaction is then passed from the reactor to an FID. In one embodiment, the elevated temperature for the reaction is in the range of 350-550° C. In another embodiment, the temperature employed for the reaction over the Ru catalyst is in the range of about 425-550° C., with a temperature of about 500° C. being of particular preference. Temperatures greater than 350° C., and even greater than 450° C. are important.

Figure 1:
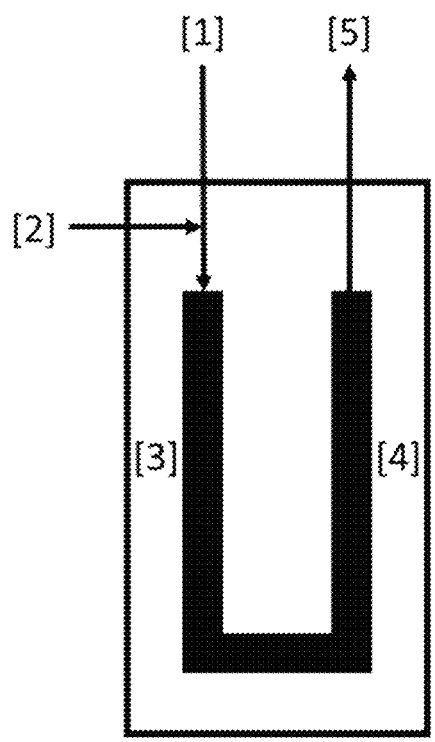
FIG. 1 is a schematic diagram of the present system.

The system as disclosed herein is schematically depicted in FIG. 1. In the system, the GC column effluent [1] is combined with $H_2$ (e.g., 10-60 cm$^3$ min$^{-1}$ but ideally 35 cm$^3$ min$^{-1}$) [2] inside the component. The $H_2$ flow needs to just be sufficient, e.g., 1 cm$^3$/min. or higher. The mixture flows through specially designed catalytic flow chambers, [3] and [4], which contain the catalyst and support structure. The catalyst is Ru metal or Ru on a catalyst support; it has been found that Ru allows for complete reduction of CO and $CO_2$ to methane, but also many organic molecules, and it is highly resistant to poisoning. The entire component is constructed in metal heated between 350-550° C. by a resistive heater with a temperature measuring device. The reactor effluent, which contains mostly $CH_4$, $H_2O$ and $H_2$, flows out of the heated reactor to the FID detector [5]. In one embodiment, the GC effluent [1] and reactor effluents [5] are on the same side of the component, as depicted in FIG. 1; these could also be on other sides of the device. The flow conditions and temperature of the reactor are optimized to ensure complete conversion of all column analytes into $CH_4$, while simultaneously mitigating deactivation of the catalyst and minimizing axial dispersion through the design of reactor packing materials and geometry. With Ru as the catalyst, the temperature is generally elevated, e.g., in the 450-550° C. range.

Figure 2:
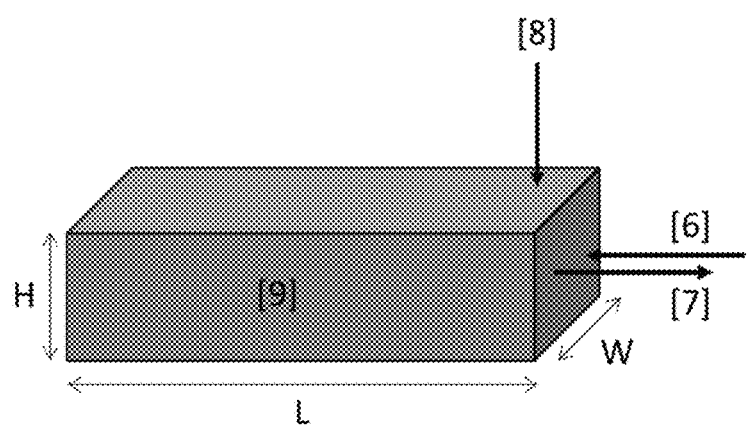
FIG. 2 is a sketch including a single block construction of the reactor.

The single block construction of the device is illustrated in FIG. 2. The GC effluent enters the component through a conduit [6] and after reaction exits through a conduit [7]. Hydrogen is added to the component through a conduit [8]. The metal block [9] contains internal channels and a Ru catalyst that allow for the efficient conversion of carbon containing molecules to methane with minimal impact on separation performance. The block can be constructed using destructive (machining) or additive (three-dimensional printing) processes to create the channels, geometries and connectivities required. The single block construction minimizes fittings leading to better flow dynamics, lower cost, ease of use and better heat transfer.

It has been found that this one-step system utilizing a Ru catalyst improves upon the prior two-step reaction scheme for generating $CH_4$ because the absence of $O_2$ in the feed stream improves the thermodynamics for the conversion to $CH_4$ over a wider range of temperatures. In addition, the need for the additional fittings, reactors, costly Pd metals, and costly flow control systems needed for the two-step process is avoided. The current system and method also eliminate the hazardous mixing of $O_2$ and $H_2$ feed streams that is unavoidable in the two-step process. The Ru-catalyst system improves upon the prior Ni-based catalyst systems because it resists poisoning, is more reactive and it converts a wider variety of carbon containing molecules (beyond CO/$CO_2$) to $CH_4$.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A system comprising a metal block containing a Ru catalyst, a first conduit from a gas chromatograph configured to pass an effluent comprising organic containing molecules to the metal block, with a hydrogen feed conduit for providing hydrogen to the metal block, where a reaction occurs to reduce the organic containing molecules to $CH_4$, and a second conduit from the metal block comprising the Ru catalyst configured to pass reaction effluent to an FID.

2. The system of claim 1, wherein the Ru catalyst comprises Ru metal or Ru on a catalyst support.

3. The system of claim 2, wherein the Ru catalyst is Ru on the catalyst support.

4. A method for the detection and quantification of organic molecules from a gas chromatograph comprising:
   passing an effluent comprising organic containing molecules from a gas chromatograph column to a metal block comprising a Ru catalyst,
   adding hydrogen to the gas chromatograph effluent,
   reacting the effluent from the gas chromatograph column in the metal block to reduce organic containing molecules to $CH_4$ by heating to a temperature of at least 350° C., and
   passing the effluent from the metal block to an FID.

5. The method of claim 4, wherein the elevated temperature for the reaction is in the range of 350-550° C.

6. The method of claim 4, wherein the temperature for the reaction is in the range of 425–550° C.

7. The method of claim 4, where the temperature for the reaction is at least 450° C.

8. The method of claim 4, wherein the temperature for the reaction is about 500° C.

9. The method of claim 4, wherein the hydrogen flow is at least 1 cm$^3$/min.

* * * * *